United States Patent
Everett et al.

(10) Patent No.: US 11,576,937 B2
(45) Date of Patent: Feb. 14, 2023

(54) METHOD OF REDUCING GUT INFLAMMATION REDUCTION IN HUMANS BY CONSUMING A HEATED PROBIOTIC COMPOSITION

(71) Applicant: NCH Corporation, Irving, TX (US)

(72) Inventors: Gabriel F. K. Everett, Mansfield, TX (US); Jordan E. Church, Dallas, TX (US); Charles J. Greenwald, Irving, TX (US); Amanda K. Rosmarin, Lantana, TX (US)

(73) Assignee: NCH Corporation, Irving, TX (US)

( * ) Notice: Subject to any disclaimer, the term of this patent is extended or adjusted under 35 U.S.C. 154(b) by 32 days.

(21) Appl. No.: 17/170,048

(22) Filed: Feb. 8, 2021

(65) Prior Publication Data
US 2021/0244775 A1    Aug. 12, 2021

Related U.S. Application Data

(60) Provisional application No. 62/970,996, filed on Feb. 6, 2020.

(51) Int. Cl.
| | | |
|---|---|---|
| *A61K 35/742* | (2015.01) | |
| *A61K 47/18* | (2017.01) | |
| *A61K 9/00* | (2006.01) | |
| *A61P 29/00* | (2006.01) | |
| *A23L 33/135* | (2016.01) | |
| *A23L 33/175* | (2016.01) | |
| *A23L 33/16* | (2016.01) | |
| *A23L 33/00* | (2016.01) | |
| *A23L 2/52* | (2006.01) | |
| *A61K 47/02* | (2006.01) | |

(52) U.S. Cl.
CPC .............. *A61K 35/742* (2013.01); *A23L 2/52* (2013.01); *A23L 33/135* (2016.08); *A23L 33/16* (2016.08); *A23L 33/175* (2016.08); *A23L 33/40* (2016.08); *A61K 9/0053* (2013.01); *A61K 9/0095* (2013.01); *A61K 47/02* (2013.01); *A61K 47/183* (2013.01); *A61P 29/00* (2018.01); *A23V 2002/00* (2013.01)

(58) Field of Classification Search
None
See application file for complete search history.

(56) References Cited

U.S. PATENT DOCUMENTS

| | | | |
|---|---|---|---|
| 4,314,995 A | 2/1982 | Hata et al. | |
| 6,051,219 A | 4/2000 | Kubota | |
| 6,327,965 B1 | 12/2001 | Tien | |
| 6,461,607 B1 | 10/2002 | Farmer | |
| 6,849,256 B1 | 2/2005 | Farmer | |
| 7,081,361 B2 | 7/2006 | Pearce, III et al. | |
| 7,736,509 B2 | 6/2010 | Kruse | |
| 8,192,733 B2 | 6/2012 | Cobb et al. | |
| 8,349,337 B1 | 1/2013 | Farmer et al. | |
| 9,011,834 B1 | 4/2015 | McKenzie et al. | |
| 9,447,376 B2 | 9/2016 | Hashman et al. | |
| 9,932,543 B2 | 4/2018 | Hashman et al. | |
| 10,610,552 B2 * | 4/2020 | Everett | A61K 35/742 |
| 10,766,799 B2 | 9/2020 | Greenwald et al. | |
| 10,897,922 B2 * | 1/2021 | Church | A61K 31/198 |
| 11,206,860 B2 * | 12/2021 | Church | A23L 33/135 |
| 2003/0165472 A1 | 9/2003 | McGrath et al. | |
| 2003/0228679 A1 | 12/2003 | Smith et al. | |
| 2004/0232069 A1 | 11/2004 | Shaffer | |
| 2005/0255092 A1 | 11/2005 | Rehberger et al. | |
| 2008/0241226 A1 | 10/2008 | Abeln et al. | |
| 2009/0041898 A1 | 2/2009 | Garbolino et al. | |
| 2009/0186057 A1 | 7/2009 | Farmer et al. | |
| 2009/0232941 A1 | 9/2009 | Farmer | |

(Continued)

FOREIGN PATENT DOCUMENTS

| | | |
|---|---|---|
| CA | 2778144 | 5/2011 |
| CN | 1528681 | 9/2004 |

(Continued)

OTHER PUBLICATIONS

Wax, R. et al. Separation of Two Functional Roles of L-Alanine in the Initiation of Bacillus subtilis Spore Generation. J of Bacteriology 94(3)522-529, Sep. 1967. (Year: 1967).*
Wuytack, E. et al. Comparative Study of Pressure and Nutrient Induced Germination of Bacillus subtilis Spores. Applied and Environmental Microbiology 66(1)257-261, Jan. 2000. (Year: 2000).*
Bergeys Manual of Systematics Archaea and Bacteria, John Wiley & Sons, Bacillus chapter 1-164, 2015. (Year: 2015).*
Soni et al., Safety Assessment of Propyl Paraben: a review of the published literature, Food and Chemical Toxicology vol. 39, 2001, p. 513-532.

(Continued)

*Primary Examiner* — Ralph J Gitomer
(74) *Attorney, Agent, or Firm* — Scheef & Stone, LLP; Robin L. Barnes

(57) ABSTRACT

A probiotic composition and method for activating probiotic spores for consumption by a human to reduce inflammation in or treat inflammatory conditions in the gut. A probiotic composition comprises a nutrient-germinant composition, one or more species of *Bacillus* spores, and optionally a food or beverage product, which are mixed or pre-mixed in any combination. A nutrient-germinant composition comprises one or more L-amino acids, optionally a source of potassium ions, and optionally one or more buffers, if the source of potassium ions is not also a buffer. A method of activating the spores comprises heating the probiotic composition or food or beverage containing the probiotic composition to a temperature range of around 42° C.-100° C., more preferably 70° C.-85° C. prior to being administered to ingested. Dosing the probiotic composition at around 1 to 4 grams per day over a treatment cycle can reduce indicators of inflammation by at least 10-20% or more.

20 Claims, No Drawings

(56) References Cited

U.S. PATENT DOCUMENTS

| | | |
|---|---|---|
| 2009/0242173 A1 | 10/2009 | Mitchell |
| 2010/0124586 A1 | 5/2010 | Becker |
| 2011/0230345 A1 | 9/2011 | Snyder et al. |
| 2011/0256216 A1 | 10/2011 | Lefkowitz |
| 2012/0034344 A1 | 2/2012 | Menon |
| 2012/0052152 A1 | 3/2012 | Armentrout |
| 2012/0100094 A1 | 4/2012 | Reuter et al. |
| 2013/0092087 A1 | 4/2013 | Bachman et al. |
| 2013/0171204 A1 | 7/2013 | DuBourdieu |
| 2014/0220662 A1 | 8/2014 | Hashman et al. |
| 2014/0295482 A1 | 10/2014 | Lyte |
| 2015/0079661 A1 | 3/2015 | Pruitt |
| 2017/0042949 A1 | 2/2017 | Penaloza-Vazquez |
| 2017/0087199 A1 | 3/2017 | Patron |
| 2017/0175070 A1 | 6/2017 | Boyette et al. |
| 2017/0246222 A1 | 8/2017 | Lewis |
| 2017/0281696 A1 | 10/2017 | Everett et al. |
| 2018/0282685 A1 | 10/2018 | Pruitt |
| 2019/0071336 A1 | 3/2019 | Greenwald et al. |
| 2019/0098915 A1 | 4/2019 | Church et al. |
| 2019/0100723 A1 | 4/2019 | Church et al. |
| 2020/0078751 A1 | 3/2020 | Schuster |

FOREIGN PATENT DOCUMENTS

| | | |
|---|---|---|
| CN | 102387703 | 3/2021 |
| WO | WO1999005310 | 2/1999 |
| WO | WO2004024865 | 3/2004 |
| WO | WO2009126473 | 10/2009 |
| WO | WO2010045541 | 4/2010 |
| WO | WO2010066012 | 6/2010 |
| WO | WO2012079973 | 6/2012 |
| WO | WO2013142792 | 9/2013 |
| WO | WO2014121302 | 8/2014 |
| WO | WO2014193746 | 12/2014 |
| WO | WO2015038892 | 3/2015 |
| WO | WO2016044661 | 3/2016 |
| WO | WO2017117089 | 7/2017 |
| WO | WO2019090065 | 5/2019 |
| WO | WO 2019/222168 | * 11/2019 |
| WO | WO2020212384 | 10/2020 |

OTHER PUBLICATIONS

Mohan, Chandra, A guide for the preparation and use of buffers in biological systems, CalBiochem Buffers, 2003; http://www.antibodybeyond.com/books/Calbiochem_Buffers_Booklet_CB0052_E.pdf, retrieved Mar. 8, 2020.

Busta, F.F. and Ordal, Z.J., Use of Calcium Dipicolinate for Enumeration of Total Viable Endospore Populations without Heat Activation, Applied Microbiology, Mar. 1964, p. 106-110, vol. 12, No. 2, American Society for Microbiology.

Carrillo-Martinez, Yarery and Setlow, Peter, Properties of Bacillus subtilis Small, Acid-Soluble Spore Proteins with Changes in the Sequence Recognized by Their Specific Protease, Journal of Bacteriology, Sep. 1994, p. 5357-5363, vol. 176, No. 17, American Society for Microbiology.

Kleijn, Roelco; Buescher, Joerg M.; Le Chat, Ludovic; Jules, Matthieu; Aymerich, Stephane; and Sauer, Uwe, Metabolic Fluxes during Strong Carbon Catabolite Repression by Malate in Bacillus subtilis, Journal of Biological Chemistry, Jan. 15, 2010, p. 1587-1596, vol. 285, No. 3, The American Society for Biochemistry and Molecular Biology, Inc.

Kong, Lingbo; Zhang, Pengfei; Wang, Guiwen; Yu, Jing; Setlow, Peter; and Li, Yong-Qing, Charactization of bacterial spore germination using phase-contrast and fluorescence microscopy, Raman spectroscopy and optical tweezers, Nature Protocols, Mar. 2011, p. 625-639, vol. 6, No. 5.

Madslien, Elisabeth H.; Granum, Per Einar; Blatny, Janet M; and Lindback, Toril, L-alanine-induced germination in Bacillus licheniformis—the impact of native gerA sequences, BMC Microbiology, published 2014, p. 1-10.

Martin, J. H. and Harper, W. J., Germination Response of Bacillus Licheniformis Spores to Amino Acids, Department of Dairy Technology, Journal of Dairy Science, Jul. 1963, p. 663-667.

Segev, Einat; Rosenberg, Alex; Mamou, Gideon; Sinai, Lior; and Ben-Yehuda, Sigal, Molecular Kinetics of Reviving Bacterial Spores, Journal of Bacteriology, May 2013, p. 1875-1882, vol. 195, No. 9.

Setlow, Peter, Summer Meeting 2013—when the sleepers wake: the germination of spores of Bacillus species, Journal of Applied Microbiology, Sep. 2013, p. 1251-1268.

Sinai, Lior; Rosenberg, Alex; Smith, Yoav; Segev, Einat; and Ben-Yehuda, Sigal, The Molecular Timeline of a Reviving Bacterial Spore, Molecular Cell, Feb. 2015, p. 695-707.

Yi, Xuan and Setlow, Peter, Studies of the Commitment Step in the Germination of Spores of *Bacillus* Species, Journal of Bacteriology, Jul. 2010, p. 3424-3433, vol. 192, No. 13.

Zhang, Pengfei; Setlow, Peter; and Li, Yongqing, Characterization of single heat-activated Bacillus spores using laser tweezers Raman spectroscopy, Optics Express, Sep. 2009, p. 16480-16491, vol. 17, No. 19.

Curran et al., Heat Activation Inducing Germination in the Spores of Thermotolerant and Thermophilic Aerobic Bacteria, Journal of Bacteriology; Apr. 1945; vol. 49, No. 4, pp. 335-346.

sigmaaldrich.com, Buffer Reference Center, Webpage [online]; Apr. 30, 2015 [date verified by web.archive.org; retrieved on Jun. 2, 2017], Retrieved from the Internet: URL: www.sigmaaldrich.com/life-science/core-bioreagents/biological-buffers/learning-center/buffer-reference-center.

Stewart et al., Commitment of bacterial spores to germinate: A measure of the trigger reaction. Biochemical Journal. Jul. 15, 1981, vol. 198, No. 1; pp. 101-106.

Boukarim et al., Preservatives in Liquid Pharmaceutical Preparations; The Journal of Applied Research; published 2009 (month unknown); vol. 9, No. 1-2; pp. 14-17.

Nagler, et al., High Salinity Alters the Germination Behavior of Bacillus subtilis Spores with Nutrient and Nonnutrient Germinants. Applied and Environmental Microbiology. Feb. 2014, vol. 80, No. 4; pp. 1314-1321.

Yasuda, Yoko and Tochikubo, Kunio, Relation between D-Glucose and L- and D-Alanine in the Initiation of Germination of Bacillus subtilis Spore, Microbio. Immunol. Oct. 1983, p. 197-207, vol. 28. No. 2.

Cutting, Simon M., Bacillus Probiotics, Food Microbiology, 2011, vol. 28, pp. 214-220.

Chedia, Aquadhi et al., Optimization of nutrient-induced germination of Bacillus sporothermodurans spores using response surface methodology, Food Microbiology, Academic Press Ltd, V. 36, N. 2, Jul. 8, 2013, pp. 320-326.

Ramirez-Peralta, Arturo et al., Effects of 1-16 sporulation conditions on the germination and germination protein levels of Bacillus subtilis spores, Applied and Environmental Microbiology Apr. 2012, V. 78, N. Apr. 8, 2012, pp. 2689-2697.

Wang, Shiwei et al., Slow Leakage of Ca-Dipicolinic Acid from Individual Bacillus Spores during Initiation of Spore Germination, Journal of Bacteriology, V. 197, N. 6, Mar. 2015, pp. 1095-1103.

Luu, Stephanie, et al., The Effects of Heat 1-16 Activation on Bacillus Spore Germination, with Nutrients or under High Pressure, with or without Various Germination Proteins, Applied and Environmental Microbiology, V. 81, N. 8, Feb. 13, 2015, pp. 2927-2398.

Katsutoshi et al., Effect of spore-bearing lactic acid-forming bacteria (*Bacillus coagulans* SANK 70258) administration on the intestinal environment, defecation frequency, fecal characteristics and dermal characteristics in humans and rats, Microbial Ecology in Health & Dis, Co-Action Publishing, SE, vol. 14, No. 1, Mar. 2002, pp. 4-13.

Bactocell Drink is Now Authorized in Europe as a Feed Additive for Swine and Poultry, news release from Lallemand Animal Nutrition, published May 15, 2013, Retrieved from the Internet on Feb. 16, 2016 at <URL: http://lallemandanimalnutrition.com/news/bactocell-drink-is-now-authorized-in-europe-as-a-feed-additive-for-swine-and-poultry/>.

Bactocell Drink on-tracks for EU authorization as a feed additive for use in drinking water for swine and poultry, news release from Lallemand Animal Nutrition, published Aug. 29, 2012, Retrieved

(56) References Cited

OTHER PUBLICATIONS from the Internet on Feb. 16, 2016 at <URL: http ://1 al lerna nda n i rn a In utritio n. com/ news/bactocel 1-d rink-a n-tracks-fo r-eu-a uthorizati on-as-a-feed- additive-for -use-i n-d rinking-water -for- swine-and-poultry/>.
Casula, G and S. Cutting. 2002. Bacillus Probiotics: Spore GermInation in the Gastrointestinal Tract. American Society for Microbiology. vol. 68, No. 5: 2344-2352.
Wikipedia, "Sodium chloride", Nov. 1, 2017, retrieved on Apr. 5, 2019 from https://en.wikipedia.org/w/index.php?title=Sodium_chloride&oldid=808219406, pp. 1-9.
Gurung, Neelam, et al., A Broader View: Microbial Enzymes and Their Relevance in Industries, Medicine, and Beyond, BioMed Research International; vol. 2013, Article ID 329121.
Yazdi, Mohammed A., et al., Characterization and cloning of the gerC locus of Bacillus subtilis 168, Journal of General Microbiology, 1990, 136, 1335-1342.
EcoBionics Biological System Data Sheet, believed to be published at least as early as 2016 (relates to Bioamp).
Maximizing Water Consumption in Poultry, Data Summary, Pacific Vet Group, International Journal of Poultry 6(7) (see also Optimizer Proven in the lab . . . .
Waites, The Effect of pH, Germinants and Temperature on the Germination of Spores of Clostridium bifermentans, Journal of General Microbiology, 1974, 80, 253-258 (Year: 1974).
Nguyen, Bacillus subtilis spores expressing the VP28 antigen; a potential oral treatment to protect Litopenaeus vannamei against white spot syndrome, FEMS Microbiilogy Letters, Sep. 1, 2014 (Sep. 1, 2014), vol. 358, pp. 202-208, p. 203.
Shearer et al., Bacterial Spore Inhibition and Inactivation in Foods by Pressure, Chemical Preservatives, and Mild Heat, Journal of Food Protection, Nov. 2000, vol. 63, pp. 1503-1510, p. 1504-1505.
Setlow, Germination of Spores of *Bacillus* Species, What We Know and Do Not Know, Journal of Bacteriologoy, Apr. 2014, vol. 196, pp. 1297-1305, p. 1298.
Joint FAO/WHO Expert Consultation on Evaluation of health and nutritional properties of probiotics in food including powder milk with live lactic acid bacteria, Cordoba, Argentina. Oct. 1-4, 2001 Oct. 1, 2001.
Chorawala, M. R., P. M. Oza, G. B. Shah. 2011. Probiotics, Prebiotics and Synbiotics: A Health Benefit Supplement. Research Journal of Pharmaceutical, Biological and Chemical Sciences vol. 2 (3): 1101-1111.
Mitsuhashi T "Effects of and L-alanine on the Swelling of Bacillus subtilis spores during germination"—Nippon suisan Gakkaishi—Bulletin of Japanese Society of Scientifici Fisheries, vol. 59, No. 5 1993 pp. 841-846.
Bader J "Spore-forming bacteria and their utilisation as probiotics" Beneficial Microbes, vol. 3, No. 1, Mar. 1, 2012 pp. 67-75.
Farzanfar, The use of probiotics in shrimp aquaculture, FEMS Immunology & Medical Microbiology, 48.2, 149-159, 2006.
Joint WHO Expert Consultation on evaluation of health and nutritional properties of probiotics in food including powder milk with live lactic acid bacteria, Cordoba Argentina Oct. 1-4, 2001.

\* cited by examiner

METHOD OF REDUCING GUT INFLAMMATION REDUCTION IN HUMANS BY CONSUMING A HEATED PROBIOTIC COMPOSITION

CROSS-REFERENCE TO RELATED APPLICATION

This application claims the benefit of U.S. Provisional Application Ser. No. 62/970,996 filed on Feb. 6, 2020.

BACKGROUND

1. Field of the Invention

This invention relates to a composition and method for germinating bacterial spores, particularly *Bacillus* spores, in a probiotic composition for human consumption to reduce inflammation, particularly inflammation in the gut.

2. Description of Related Art

Recent scientific advances have shed light on the significance of the relationship between human gut bacteria (the microbiome) and general health. The human microbiome is a product of our genetics, our diets, and our environment. Probiotics may be used to alter the human microbiome. Estimates put the average number of species in an individual's microbiome at 160 different species. Probiotics may be used to modulate the species present in the human microbiome in order to regulate the digestive system and bolster the immune system. Specifically, new evidence has shown that probiotics may decrease the inflammatory response and can improve clinical symptoms in patients suffering from inflammatory bowel diseases such as ulcerative colitis (UC) and Crohn's disease (CD). Generally, UC and CD are characterized by chronic inflammation of the gastrointestinal (GI) tract. In the case of UC, inflammation occurs predominantly in the large intestine and rectum whereas in CD, inflammation can occur in any part of the digestive tract, but mostly affects the small intestine.

Probiotics are live, non-pathogenic bacteria that provide health benefits when they are consumed. Probiotics have been widely used in humans as a digestive supplement delivered as a capsule, in a powder, and in various food products (e.g. yogurt, juice, etc.). Probiotic bacteria may include species of lactic acid bacteria (*Lactobacillus*), *Bifidobacterium*, and *Propionibacterium*. Species of *Bacillus* are also common as probiotics. In the case of *Bacillus* species as probiotics (e.g. *B. subtilis*), the bacteria are supplied as spores. Spores are formed by specific species of bacteria that have the ability to transition into a dormant spore stage if environmental conditions are unfavorable. Spores are naturally dehydrated, are stable for extended periods of time, and are resistant to environmental stresses (such as heat, salt, pH, etc.).

In general, probiotics claim to exert their health benefits in the intestine, but most probiotic bacteria available on the market currently will die in the harsh gastric environment before reaching the intestine. In most cases, traditional probiotics which survive the stomach will: 1) transiently colonize and have an effect only in the large intestine, or 2) will pass right through the digestive tract with no benefits. Spores, on the other hand, are more favorable as probiotics than non-spore forming bacteria found in traditional probiotics because they show increased resistance to stomach conditions. Once in the intestinal tract, spores will eventually germinate in the large intestine or the colon. In order for probiotics to effectively treat symptoms of inflammatory bowel diseases like UC and CD, they must be active in the digestive compartment where inflammation occurs. For example, if CD is caused by inflammation in the small intestine, probiotics must function there to relieve symptoms.

Germination is a complex process in which spores are revived from the dormant state so they may develop into a fully vegetative growth state. The first step is one by which spores are activated and are induced to germinate, typically by an environmental signal called a germinant. This signal can be a nutrient such as an L-amino acid or potassium ions (e.g. KCl). Nutrient germinants bind to receptors in the inner-membrane of the spore and are required to initiate germination. The addition of heat, such as that in a hot beverage (tea, coffee, etc.) or human body temperature (approx. 37° C.) speeds this step up.

The germinant signal initiates an irreversible cascade of events, also known as commitment. The commitment process can take as little as 2 minutes. As germination progresses, the spore rapidly hydrates. As the spore absorbs water it consequently loses its refractivity. This loss of refractivity towards the end of the first phase in the germination process allows spore germination to be observed via phase-contrast microscopy. The initial phase is typically complete within 30 to 60 minutes depending on the temperature. The second phase of germination is an outgrowth step in which the spore's metabolic, biosynthetic, and DNA replication/repair pathways initiate. The outgrowth period includes a ripening period in which no morphological changes (such as cell growth) occur, but the spore's molecular machinery (e.g. transcription factors, translation machinery, biosynthesis machinery, etc.) is activated. This period can vary in length based on the initial resources that are packaged with the spore during the process of sporulation.

It is known that spores can be induced to germinate via heat-activation. Spores of various *Bacillus* species have been heat-activated at strain specific temperatures (e.g. *B. subtilis* spores can be heat-activated at 75° C. for 30 minutes while *B. licheniformis* spores can be heat-activated at 65° C. for 20 minutes). The heat-activation is believed to cause a transient, reversible unfolding of spore proteins. Heat-activated spores can then be germinated for additional time in germination buffers containing nutrient germinants, such as L-alanine. If no nutrient germinant, such as L-alanine, is provided they will refold and effectively reverse the germination process, returning to their pre-heated, non-germinated state.

It is also known that germination can occur at ambient temperatures (near typical room temperature) without heat-activation and with a germination buffer containing nutrients, but the process usually takes longer than with heat-activation. For example, *B. licheniformis* and *B. subtilis* spores will germinate at 35° C. or 37° C., respectively, but it takes a longer period of time (e.g. 2 hours) in a germination buffer containing nutrient germinants. Additionally, non-heat-activated spores of *B. subtilis* have been known to have been germinated in non-nutrient germinant conditions (e.g. $CaCl_2$)+$Na_2DPA$) for an extended period of time.

It is also known to combine the use of heat activation and a nutrient germinant to germinate spores in a two-step process in laboratory settings. The spores are first heat activated by incubating for a period of time (e.g. 30 minutes) at a temperature in the range of 65-75° C. (this specific temperature is species dependent).

Then, the spores are transferred into a buffer solution that contains a nutrient germinant, such as L-alanine.

Probiotics for human consumption are available as capsules and as food products (e.g. yogurt, beverages, etc.). Although there are several examples of probiotics on the market, including probiotics added to heated food or beverage products as described in Applicant's U.S. Pat. No. 10,897,922, there are none that include an activating component to germinate probiotic spores for improved efficacy when administered to or ingested by a human to specifically reduce inflammation or treat inflammatory conditions or diseases in the digestive tract and particularly the intestines. There is a need for a rapid spore incubation and activation method that will allow generation of active *Bacillus* species in a single step for administration to or ingestion by human having an inflammatory condition or disease that will allow the *Bacillus* to begin germination at a time of administration or ingestion, survive through the stomach, and be vegetative when the bacteria reach the intestinal tract to reduce inflammation, particularly to treat or improve the symptoms of UC or CD.

SUMMARY OF THE INVENTION

Preferred embodiments of the invention comprise a probiotic composition comprising a spore composition and a nutrient germinant composition and a method for activating the probiotic spores with the nutrient germinant composition for the purpose of reducing intestinal inflammation indicative of inflammatory bowel diseases, including CD and UC. One preferred method comprises providing a nutrient germinant composition and a spore composition comprising *Bacillus* spores that may be heat activated before consumption (by administration or ingestion) by a human. According to another preferred embodiment, the two components or compositions (bacterial spores and nutrient germinants) may be provided as separate components that are combined together in a specified amount of water, preferably hot water, immediately before consumption.

According to another preferred embodiment, the two compositions may be provided as pre-mixed ingredients (nutrient germinant composition and spores in a single composition). Such pre-mixed composition may be in a single serve packet to be added to warm food products (e.g. tea, soup, sauce gravy, etc.) or cold food products (juice, yogurt, ice cream, etc.).

According to other preferred embodiments, spores can be heat-activated in the presence of nutrient germinants according to the methods and compositions that are described in U.S. patent application Ser. No. 15/479,773 (U.S. Pat. No. 10,610,552), which is incorporated herein by reference. According to other preferred embodiments, probiotic spores and nutrient germinant compositions may be mixed with food or beverage products according to the compositions and methods that are described in U.S. patent application Ser. No. 16/178,905 (U.S. Pat. No. 10,897,922), which is incorporated herein by reference.

A nutrient-germinant composition according to one preferred embodiment of the invention comprises one or a combination of many L-amino acids, optionally D-glucose (which increases the binding affinity of L-amino acids for their cognate receptors in the spore coat), and a neutral buffer such as a phosphate buffer. It is preferred not to include an industrial preservative for treatment of inflammatory conditions or diseases, but one may optionally be included, such as the commercially available Kathon/Lingaurd CG (which has active ingredients comprising methyl chloro isothiazolinone and methyl isothiazolinone). Preservatives such as propylparaben or methylparaben (or preferably a combination of the two) or other GRAS (Generally Regarded As Safe under U.S. Federal standards) preservatives may also be optionally used, but are preferably omitted. A nutrient-germinant composition according to another preferred embodiment of the invention comprises HEPES sodium salt (a biological buffer to provide the proper pH for spore germination). According to another preferred embodiment, the composition also comprises a source of potassium ions, such as potassium chloride or monopotassium phosphate or dipotassium phosphate. According to another preferred embodiment, the composition includes both D-glucose and D-fructose. According to yet another preferred embodiment, the composition does not include D-glucose or D-fructose.

According to another preferred embodiment, a spore composition or spore formulation comprises one or more species of *Bacillus* in spore form. The spore composition preferably comprises a dry, powder blend of 40-60% salt (table salt) and 60-40% bacteria spores.

According to another preferred embodiment, when a nutrient germinant composition is premixed with spores or a spore composition (preferably one according to a preferred embodiment of the invention) comprising one or more *Bacillus* species, the premixed composition also comprises a germination inhibitor, such as NaCl, industrial preservatives (preferably not included, but optionally may be included), or D-alanine, in combination with any of the previously described composition ingredients. It is not necessary to include a germination inhibitor if the premixed probiotic composition is in solid or powdered form, but is preferred is they are in a fluid form comprising water. The germination inhibitor prevents the spores from germinating prematurely in the probiotic composition with the nutrient germinants. Alternatively, bacterial spores may be separately provided and added to a nutrient-germinant composition according to the invention at the point-of-consumption.

According to another preferred embodiment, a nutrient germinant composition and spore composition (either separate or pre-mixed) are added to a food or beverage product prior to consumption. Most preferably, the food or beverage product is one that is heated to a temperature as described in preferred methods of the invention prior to consumption. Alternatively, the food or beverage product may be cold or at room temperature at the time of consumption.

According to one preferred embodiment of the invention, a probiotic composition and method is provided for pre-activating probiotic spores before consumption so that they germinate and are active in the small intestine to effectively alleviate inflammation that is the result of inflammatory bowel diseases. The spores are preferably pre-activated by heating, preferably in a range of 42-100° C. for a period of time (an incubation period) prior to consumption. Most preferably, the food or beverage product (just prior to or just after adding the spores and nutrient germinant compositions or premixed composition) is heated to this temperature range and then consumed after the incubation period. The incubation period preferably ranges from 2-10 minutes.

The preferred embodiments of the invention have are particularly useful in treating or reducing the symptoms of inflammatory conditions or diseases, specifically bowel or intestinal tract conditions or diseases, including as ulcerative colitis and Crohn's disease.

DETAILED DESCRIPTION

According to one preferred embodiment, a probiotic composition comprising around 0.001 to 5% (more preferably around 0.02 to 1%, most preferably around 0.025 to 0.5%) of a spore composition and around 95 to 99.999% (more preferably around 99 to 99.98%, most preferably around 99.5 to 99.975%) of a nutrient germinant composition, both by weight of the probiotic composition, is administered to or ingested by a human to reduce inflammation, particularly to reduce levels of C-reactive protein as an indicator of inflammation level in the human. Preferred spore compositions and nutrient germinant compositions are further described herein. Most preferably, all ingredients in the probiotic composition are GRAS (generally regarded as safe for human consumption under U.S. federal standards). A dose of the probiotic composition is around 1 to 5 g, more preferably around 3 to 4 g, which is administered or ingested by the human periodically over the course of a treatment cycle. A dose is administered or ingested preferably around 1 to 3 times per day, more preferably around 1 to 2 times per day. A treatment cycle preferably lasts at least 6 months, more preferably at least 4 months, but may be longer or shorter. The probiotic composition may be mixed with a food or beverage product prior to being administered or ingested. Most preferably, the food or beverage product is one that is heated to a temperature between 42° C. and 100° C. or to which a hot fluid (such as water or milk) at a temperature between 42° C. and 100° C. is added prior to consumption.

The compositions and methods of the invention are particularly well suited for administration to or ingestion by humans having Crohn's disease or ulcerative colitis. The probiotic compositions and probiotic food and beverage compositions according to preferred embodiments are capable of reducing inflammation as indicated by a reduction in levels of C-reactive protein by around 1 to 32%, more preferably around 10-20% or more when dosed according to preferred methods of the invention compared to baseline C-reactive protein levels prior beginning use of the probiotic composition. When a person's baseline pre-treatment level of C-reactive protein is less than around 1,000 pg/mL (typically considered a "healthy" level), the probiotic compositions and probiotic food and beverage compositions according to preferred embodiments are capable of reducing inflammation as indicated by a reduction in levels of C-reactive protein by around 10-20% when dosed according to preferred methods of the invention. When a person's baseline pre-treatment level of C-reactive protein is greater than around 1,000 pg/mL, the probiotic compositions and probiotic food and beverage compositions according to preferred embodiments are capable of reducing inflammation as indicated by a reduction in levels of C-reactive protein by around 10-32%, more preferably 20-32%, and most preferably by around 23-31% (or 27%+/−4%) when dosed according to preferred methods of the invention.

Nutrient Compositions

Described herein are preferred embodiments of nutrient compositions (or nutrient germinant compositions) that may contain one or more L-amino acids, D-glucose, D-fructose, a biological buffer, and a potassium ion source. All components in the nutrient formulation must be Generally Regarded as Safe (GRAS) for human consumption by the United States Food and Drug Administration. At the time of filing this application, the components described herein have been deemed GRAS, but other ingredients that are currently or are later deemed GRAS may also be used.

According to one preferred embodiment, the nutrient germinant composition can include one or more L-amino acids. Preferred L-amino acid(s) included in the nutrient formulation are L-alanine, L-asparagine, L-valine, and/or L-cysteine. The choice of L-amino acids is determined by the species of Bacillus used in the probiotic formulation. The L-amino acids can be provided in the form of any suitable source, such as their pure forms and/or a hydrolysate of soy protein.

According to another preferred embodiment, the nutrient germinant composition can optionally contain an amount of D-glucose and/or D-fructose. The choice of sugar is determined by the species of Bacillus used in the probiotic formulation. When Bacillus subtilis is used as the bacteria, it is preferred not to use any added sugars.

According to another preferred embodiment, the nutrient germinant composition can optionally contain one or more sources of potassium ions. Preferably, dipotassium phosphate, monopotassium phosphate, or KCl can be included as a source of potassium ions in the nutrient formulation. The inclusion of potassium ions is determined by the species of Bacillus used in the probiotic formulation. When Bacillus subtilis and/or Bacillus licheniformis are used as the bacteria, it is preferred to include a source of potassium ions. Most preferably, dipotassium phosphate or monopotassium phosphate are used as sources of potassium and can also act as a buffer, making it unnecessary to add a separate buffer. Although potassium chloride may also be used, it is preferred not to include it because it can be overly salty tasting to some humans, making the probiotic composition unpalatable, particularly when used in a beverage.

Additionally, a combination of one or more of potassium chloride, monopotassium phosphate, and dipotassium phosphate may be used. When added to a food product, the inclusion of potassium chloride and its salty taste may be beneficial in enhancing the flavor of the food, but it is preferred to use it in combination with a potassium phosphate.

According to another preferred embodiment, the nutrient germinant composition can optionally contain one or more biological buffers. The biologic buffer is a buffer that can buffer the nutrient formulation and/or nutrient-spore formulation, to maintain the formulation at the proper pH for spore germination (about pH 6-8). Preferred biologic buffers include, but are not limited to, a phosphate buffer or a HEPES sodium salt. According to another preferred embodiment, monosodium phosphate and disodium phosphate, preferably used together, can be included in the nutrient formulation as buffers. According to another preferred embodiment, a HEPES buffer may be used.

According to another preferred embodiment, the nutrient composition is any one of the nutrient compositions described in U.S. patent application Ser. No. 15/479,773, incorporated herein by reference. According to another preferred embodiment, the food or beverage product with probiotic spores and nutrient germinants is any one of the compositions described in U.S. patent application Ser. No. 16/178,905, incorporated herein by reference.

According to yet another preferred embodiment, a nutrient composition may contain ingredients in one or more of the above-referenced categories of ingredients and may contain one or more ingredients from within those categories.

A nutrient-germinant composition according to one preferred embodiment of the invention comprises one or more L-amino acids, D-glucose (which increases the binding affinity of L-amino acids for their cognate receptors in the spore coat and is optional), D-Fructose (optional, depending on bacteria species), a biological buffer to provide the proper pH for spore germination (such as HEPES sodium salt, a phosphate buffer, or a Tris buffer), an optional source of potassium ions (such as dipotassium phosphate, monopotassium phosphate, or KCl), and an optionally a natural osmoprotectant compound (such as ectoine). Preferred L-amino acids include L-alanine, L-asparagine, L-valine, and L-cysteine. In a further embodiment of the concentrate composition, L-amino acids can be provided as a hydrolysate of soy protein. An optional preservative may also be used. In another preferred embodiment, the composition comprises both D-glucose and D-fructose. It is most preferred to include a source of potassium ions, such as dipotassium phosphate, monopotassium phosphate, or KCl, when both D-glucose and D-fructose are used. The use of D-fructose, a combination of D-glucose and D-fructose, and a potassium ion source are dependent on the species of bacteria as will be understood by those of ordinary skill in the art. If a preservative is used, it is preferred to use a preservative that is pH compatible with the composition, which has a relatively neutral pH.

According to one preferred embodiment, a nutrient germinant composition comprises around 45-55% of an L-amino acid (e.g. L-alanine) and 45-55% dipotassium phosphate. Alternatively, monopotassium phosphate could be used, but more would be required to achieve the same level of potassium, so dipotassium phosphate is preferred. According to another preferred embodiment, a nutrient germinant composition comprises 4-8% of an L-amino acid (e.g. L-alanine), 4-8% dipotassium phosphate, and 80-90% flavoring (natural or artificial). As another alternative, the flavoring may be included in the spore composition, with adjustments to the amount of spores and salt described below accordingly. According to another preferred embodiment, a nutrient germinant composition comprises only one or more L-amino acids and dipotassium phosphate and optionally a flavoring (natural or artificial). According to another preferred embodiment, nutrient germinant composition comprises 40-45% of an L-amino acid (e.g. L-alanine), 40-45% potassium (such as potassium chloride, monopotassium phosphate, or dipotassium phosphate), 4-6% monosodium phosphate (optional if the source of potassium is a phosphate), and 10-12% disodium phosphate (optional if the source of potassium is a phosphate). According to another preferred embodiment, nutrient germinant composition comprises 4-6% of an L-amino acid (e.g. L-alanine), 4-6% potassium phosphate, 25-30% flavor (natural of artificial), 60-70% prebiotic (e.g. inulin), and 2-3% of a flavor enhancement (e.g. citric acid). As another alternative, the flavoring and/or flavor enhancement may be included in the spore composition, with adjustments to the amount of spores and salt described below accordingly.

Spore Formulations

Preferred embodiments of spore formulations or spore compositions include one or more *Bacillus* species in spore form, including but not limited to, *Bacillus licheniformis, Bacillus subtilis, Bacillus amyloliquiefaciens, Bacillus polymyxa, Bacillus thuringiensis, Bacillus megaterium, Bacillus coagulans, Bacillus lentus, Bacillus clausii, Bacillus circulans, Bacillus firmus, Bacillus lactis, Bacillus laterosporus, Bacillus laevolacticus, Bacillus polymyxa, Bacillus pumilus, Bacillus simplex, Bacillus sphaericus, Bacillus sonorensis, Bacillus, horneckiae, Bacillus axarquiensis, Bacillus mucilaginosus, Bacillus olivae*, and any combinations thereof. All strains in the probiotic formulation must be Generally Regarded as Safe (GRAS) for human consumption by the United States Food and Drug Administration. At the time of filing this application, several, although not all, of the above mentioned strains have been deemed GRAS. Any *Bacillus* species subsequently determined to be GRAS are included here as suitable for use with embodiments of the invention.

Preferred spore formulations can contain 1-20 species and/or strains of *Bacillus* spores, including any individual number or subrange therein. Spore formulations may also include more than 20 species and/or strains, but it is preferred that they do not include more than 20. More preferably, the composition comprises 2 to 12 *Bacillus* species and/or strains and most preferably, the composition comprises 2-5 *Bacillus* species and/or strains. Preferred *Bacillus* combinations include (1) *subtilis* and *coagulans*; (2) *subtilis* and *licheniformis*; (3) *subtilis* and *clausii*; (4) *subtilis* and *indicus*; (5) *coagulans* and *licheniformis*; and (6) *subtilis, licheniformis*, and *coagulans*. According to one preferred embodiment, a spore formulation can contain 3 strains of *Bacillus* bacteria. According to another preferred embodiment, 2 strains of the *Bacillus* bacteria can each be a different strain of the species *Bacillus licheniformis* and the third strain is a species of *Bacillus subtilis*. According to another preferred embodiment, about 80% of the formulation can be *Bacillus licheniformis* (40% of each strain) and 20% of the spores in the spore formulation can be *Bacillus subtilis*. *Bacillus subtilis* and *Bacillus licheniformis* are a particularly preferred bacteria since they requires fewer nutrient germinant composition ingredients and have been shown to germinate well (>95%) in only L-alanine and dipotassium phosphate according to a preferred nutrient germinant composition. According to another preferred embodiment, the spores of the strain(s) included in the spore formulation can be mixed with water or other suitable carrier and/or organic salts.

Most preferably, the *Bacillus* species that can be contained in the spore formulations can produce and/or be capable of producing one or more enzymes including, but not limited to, proteases, amylases, lipases, glycosidases, cellulases, esterases, and xylanases. Tests and assays for determining the production of such enzymes from a *Bacillus* species are generally known in the art and to one of ordinary skill in the art.

According to one preferred embodiment, the spore formulation can contain about 0.1% to 90% by weight spores, along with salt or other suitable carrier, such as sodium bicarbonate, or maltodextrin, or salt, or a combination thereof. According to another preferred embodiment, the spore composition comprises a dry, powder blend of 40-60% salt (table salt) and 60-40% *Bacillus* spores. The spore formulation can be and/or include a powder or other dry form (e.g. spray-dried form of a liquid spore concentrate, or lyophilized spore formulation) containing spores.

According to another preferred embodiment, the total concentration of spores in the spore formulation (or in a premixed probiotic composition comprising both spores and a nutrient germinant composition) can range from about $1 \times 10^5$ CFU/mL or spores/g to $1 \times 10^{14}$ CFU/mL or spores/g or any specific concentration or range therein. The total preferred concentration of spores in the spore formulation can be about 1, 1.125, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, or $9.75 \times 10^5$, $10^6$, $10^7$, $10^8$, $10^9$, $10^{10}$, $10^{11}$, $10^{12}$, $10^{13}$, or $10^{14}$ CFU/mL or spores/g or any range or other individual value therein.

According to another preferred embodiment, any one specific spore species can be present in the spore formulation (or in a premixed probiotic composition comprising both spores and a nutrient germinant composition) at a concentration that can range from about $1 \times 10^5$ CFU/mL to $1 \times 10^{14}$ CFU/mL or any specific range therein. The preferred concentration of any one specific spore species present in the preferred embodiments of spore formulations (or in a premixed probiotic composition comprising both spores and a nutrient germinant composition) according to the invention can be about 1, 1.125, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, or 9.75×$10^5$, $10^6$, $10^7$, $10^8$, $10^9$, $10^{10}$, $10^{11}$, $10^{12}$, $10^{13}$, or $10^{14}$ CFU/mL or spores/g or any range or other value therein. Preferably, the spore formulation is biodegradable. According to another preferred embodiment, the concentrated spore formulation (or a pre-mixed probiotic composition comprising both spores and a nutrient germinant composition) can contain about 1-9×$10^9$ or $10^{10}$ CFU/mL or spores/g. According to another preferred embodiment, the concentrated spore formulation (or a pre-mixed probiotic composition comprising both spores and a nutrient germinant composition) can contain about $10^{10}$ CFU/mL or spores/g.

Mixing Probiotic Compositions, Pre-Mixed Compositions, and Food or Beverage Products According to one preferred embodiment, a probiotic composition according to the invention comprises a nutrient composition (preferably according to a preferred embodiment of the invention) and a spore formulation or spore containing composition (preferably according to a preferred embodiment of the invention), and optionally one or more prebiotics and/or powdered flavorings that are mixed together. The prebiotics may include, but are not limited to, prebiotic fiber (inulin), prebiotic sugar (raffinose), and other knowns prebiotics. Most preferably, spores and nutrient-germinant ingredients are premixed together at manufacturing/packaging. According to one preferred embodiment, a premixed probiotic composition comprises around 0.01 to 5% (more preferably around 0.1 to 1%, most preferably around 0.2 to 0.3%) of a spore composition and around 99.99 to 95% (more preferably around 99 to 99.9%, most preferably around 99.8 to 99.7%) of a nutrient germinant composition, both by weight of the probiotic. According to another preferred embodiment, a premixed probiotic composition comprises around 0.001 to 5% (more preferably around 0.02 to 1%, most preferably around 0.025 to 0.5%) of a spore composition and around 95 to 99.999% (more preferably around 99 to 99.98%, most preferably around 99.5 to 99.975%) of a nutrient germinant composition, both by weight of the probiotic composition. According to another preferred embodiment, a premixed probiotic composition comprises 0.1-1% probiotic spores, 40-50% of an L-amino acid (e.g. L-alanine), and 40-50% dipotassium phosphate. According to another preferred embodiment, a premixed probiotic composition comprises 0.1-1% probiotic spores, 4-8% of an L-amino acid (e.g. L-alanine), 4-8% dipotassium phosphate, and 80-90% of flavoring. According to another preferred embodiment, a premixed probiotic composition comprises 0.1-1% probiotic spores, 4-8% of an L-amino acid (e.g. L-alanine), 4-8% dipotassium phosphate, 20-30% of a flavor (natural or artificial), 60-70% prebiotic (e.g. inulin), and 2-4% of a flavor enhancement (e.g. citric acid). According to another preferred embodiment, a premixed probiotic composition comprises 0.1-1% probiotic spores, 40-45% of an L-amino acid (e.g. L-alanine), 40-45% potassium (such as potassium chloride, monopotassium phosphate and/or dipotassium phosphate), 4-6% monosodium phosphate (optional if a phosphate is used as the source of potassium), and 10-12% disodium phosphate (optional if a phosphate is used as the source of potassium). According to other preferred embodiments, a probiotic composition may be mixed at the time of use from a separate spore composition and nutrient germinant composition to provide a mixed probiotic composition in the same proportions as described herein for premixed probiotic compositions.

According to another preferred embodiment, a premixed probiotic composition is packaged in a single dose amount comprising around 1-5 g of probiotic composition, more preferably around 2-4 g, most preferably around 3-3.5 g. Most preferably, the premixed probiotic composition is in powdered form so that it is easy to mix with a food or beverage product prior to consumption. Additionally, when in a solid or powdered form, it is not necessary to add any germination inhibitors or preservatives to prevent the spore from germinating in the packaging prior to use. Most preferably each single dose of probiotic composition is added to an amount of a food or beverage product. According to other preferred embodiments, a probiotic composition may be mixed at the time of use from a separate spore composition and nutrient germinant composition to provide a mixed probiotic composition in the same dose amounts as described herein for premixed probiotic compositions.

According to another preferred embodiment, a probiotic composition may be premixed with a food or beverage product at the point of manufacturing/packaging. Most preferably, the food or beverage product is one that is a fluid at consumption (such as water, coffee, tea, hot chocolate, or soup) or a semi-fluid or thickened (such as pudding, yogurt, or smoothie) food or beverage product to allow the probiotic composition to be easily mixed, which may aid in masking the taste if a flavoring is not included in the probiotic composition. The food or beverage product or premixed probiotic food or beverage composition may also be in solid or powdered form to which a potable fluid (such as water or milk) is added prior to consumption. The preferred amount of fluid or semi-fluid food or beverage product, or amount of potable fluid added to a solid or powdered food or beverage product, for each dose of probiotic composition is 4-12 oz, more preferably 6-10 oz, and most preferably 7-9 oz, that is easily consumed in a short period of time. Most preferably, the probiotic composition is added to a food or beverage product that is warmed or heated prior to consumption, preferably to a temperature range of 42° C. to 100° C. or at any temperature or subrange therein. Most preferably, the probiotic composition is allowed to incubate in the heated food or beverage for 2-10 minutes prior to consumption. It is also preferred that the entire dose of probiotic composition (or the entire probiotic food or beverage composition) is consumed within 3-60 minutes, more preferably 3-20 minutes of being mixed together (if not premixed as a probiotic food or beverage composition) or heated (if heated).

According to another preferred embodiment, a spore composition and nutrient-germinant composition are separately packaged and mixed together at the point of consumption, and are preferably mixed with a food or beverage product, prior to consumption, to form a probiotic food or beverage composition. The amounts and proportions when mixed from separate components is preferably the same as described herein for premixed components. The food or beverage product (prior to adding the spore composition and nutrient-germinant composition) or the probiotic food or beverage composition is preferably heated a temperature range of 42° C. to 100° C. or at any temperature or subrange therein prior to consumption. Most preferably, the spore composition and nutrient-germinant composition are in powdered or dry form, but either or both may also be a liquid.

According to another preferred embodiment, a probiotic composition (either premixed or as separate components) may be added to a specified amount of water or other potable liquid as a single-serve probiotic orally consumed "shot". Preferably hot water/liquid in a temperature range of 42° C. to 100° C. or at any temperature or subrange therein is used in a single-serve probiotic "shot." A shot preferably comprises 1-10 oz. of fluid, preferably water, but other liquids may also be used, and 1-5 weight of probiotic composition, more preferably 6-8 oz. of fluid and 3-4 weight of probiotic composition. According to another preferred embodiment, room temperature or cold water/liquid may also be used for a single-serve probiotic "shot".

When a probiotic composition is added to a fluid or semi-fluid food or beverage product (or when a potable fluid is added to a solid or powdered food or beverage product or probiotic food or beverage composition, such as powdered hot chocolate to which water or milk are added), the probiotic food or beverage composition preferably comprises one or more L-amino acids in the weight range of 0.165-0.275 g/8 oz. dose, more preferably 0.198-0.242 g/8 oz. dose, and most preferably 0.209-0.231 g/8 oz. dose each; an optional but preferred source of potassium ions; and a buffer, such as a phosphate buffer. A source of potassium ions may include KCl preferably in a weight range of 0.165-0.275 g/8 oz. dose, more preferably 0.198-0.242 g/8 oz. dose, and most preferably 0.209-0.231 g/8 oz. dose; dipotassium phosphate preferably in a weight range of 0.1725-0.2875 g/8 oz. dose, more preferably 0.207-0.253 g/8 oz. dose, and most preferably 0.2185-0.2415 g/8 oz. dose; and/or monopotassium phosphate preferably in a weight range of 0.17-0.29 g/8 oz. dose, more preferably 0.2-0.26 g/8 oz. dose, and most preferably 0.21-0.24 g/8 oz. dose. When monopotassium phosphate or dipotassium phosphate is used as a source of potassium ions, it can also act as a buffer, making it unnecessary to add a separate buffer. Other buffers may comprise monosodium phosphate in a weight range of 0.0225-0.0375 g/8 oz. dose, more preferably 0.027-0.033 g/8 oz. dose, and most preferably 0.0285-0.0315 g/8 oz. dose and/or disodium phosphate in a weight range of 0.045-0.075 g/8 oz. dose, more preferably 0.054-0.066 g/8 oz. dose, and most preferably 0.057-0.063 g/8 oz. dose. Other optional ingredients in probiotic food or beverage composition comprise D-glucose (optional) and/or D-fructose (optional) in the weight range of 0.32-0.53 g/8 oz. dose, more preferably 0.38-0.47 g/8 oz. dose, and most preferably 0.4-0.44 g/8 oz. dose each. The amounts per 8 oz. dose are per 8 fluid ounces of the food or beverage product. The amounts may be adjusted for smaller or larger amounts of food or beverage product to provide a probiotic dose within the preferred ranges herein with each dose of food or beverage product to be consumed.

According to another preferred embodiment, a premixed probiotic food or beverage composition (containing spores, nutrient germinants and food/beverage) may further comprise one or more germination inhibitors and/or preservatives or one or both of these ingredients may be omitted. It is preferred not to include a germination inhibitor or preservative in a powdered or solid probiotic composition or a powdered or solid premixed probiotic food or beverage composition (such as powdered hot chocolate premixed with spores and powdered nutrient germinant composition at manufacturing/packaging). However, if in a liquid form or in a premixed probiotic food or beverage composition (one where spores, a nutrient composition, and food or beverage are premixed at the point of manufacturing/packaging) comprising water, it is preferred to have a germination inhibitor or preservative to prevent premature germination of the spores in the packaging prior to consumption. Preferred germination inhibitors or preservatives include NaCl, D-alanine, or preservatives. As most food or beverage products would already contain a preservative, it is generally not necessary to add a separate germination inhibitor or preservative when making a premixed probiotic food or beverage composition, but they may be added if needed. Such germination inhibitors or preservatives maintain the spores in an inactive state and prevent premature germination of the spores prior to their activation when added to a heated food or beverage product or when heated by body temperature after ingestion or administration. Although a chemical preservative may also be used, it is preferred not to use one for human administration or ingestion.

According to another preferred embodiment, a probiotic composition may be made into a tablet or pill form to be swallowed whole or chewed, without requiring the probiotic composition to be added to a food or beverage product. According to another preferred embodiment, the probiotic composition may comprise a nutrient composition and a separate spore composition, in solid, powered, or liquid form, or a combination thereof, that are (1) mixed together just prior to administering or ingesting, with or without any separate food or beverage product, or (2) are separately administered or ingested, with or without any separate food or beverage product for either component, at substantially the same time.

According to one preferred method of providing probiotics, the nutrient/spore composition are added to a food/drink product that is administered to or ingested by a human. Most preferably, the nutrient composition and spore formulation are one of the above described embodiments. The formulation would preferably be provided as a powder (with a first composition comprising probiotic bacteria in spore form and a second composition comprising nutrient germinant ingredients, which may be premixed together as a premixed probiotic composition or may be in separate packets, containers, tablets, capsules, or the like) that is added to either a hot food product (preferably tea, soup, sauce, coffee, hot chocolate, gravy, hot pudding, but other heated fluid, semi-solid, or solid food or beverage products may be used) or a cold (or room temperature) food product (preferably yogurt, ice cream, juice, smoothies, pudding, gelatin, milkshakes, iced coffee, iced tea, but other cold or room temperature fluid, semi-solid, or solid food or beverage products may be used) prior to consumption. Most preferably, the probiotic spore composition and nutrient germinant components are pre-mixed together as a probiotic composition, but may also be separately added to the food product. Additionally all three components, spores (or a spore composition), nutrient germinant composition, and food/beverage product), may be pre-mixed together as a probiotic food or beverage composition at the time of manufacturing/packaging.

According to one preferred embodiment, the two components (bacterial spores and nutrient germinants) may be provided as dry or powdered components in an automatic coffee maker pod (e.g. Keurig®, Nespresso®, Tassimo®, etc.) containing tea, coffee, hot chocolate, cider, soup, or another food or beverage product as a premixed probiotic food or beverage composition. According to another preferred embodiment, the ingredients may be provided as mixed ingredients (nutrient germinant composition and spores) in a single serve packet to be added to tea or another food or beverage product, mixed components (nutrient germinant composition and spores) in a single bag containing tea or another food or beverage product, or as separated components in separate tea bags (e.g. two bags containing any combination of the nutrient germinant composition, spores, and tea) or other container for other food or beverage products.

Preferred food and beverage products comprise steeped teas, soups, gravies, sauces, hot chocolate, coffee, and other products, particularly heated liquids and fluids. Cold food products, such as juices, yogurt, pudding, smoothies, and milkshakes may also be used.

According to another preferred embodiment, a probiotic food or beverage composition (either as a premixed composition or as separate components that are mixed together at or near the time of consumption) comprises around 0.0001 to 0.1 g/oz (more preferably around 0.0001 to 0.01 g/oz) of the spore composition and around 1 to 4 g/oz (more preferably around 2 to 4 g/oz) of the nutrient germinant composition, both amounts per ounce of the final probiotic food or beverage composition to be consumed (after adding water, milk, or any other fluid that would be added prior to consumption, such as for a powdered coffee, tea, or hot chocolate probiotic beverage composition).

Consumption by a Human

According to one preferred embodiment, a person having an inflammatory condition, such as Crohn's disease or ulcerative colitis, then ingests the probiotic food or beverage composition containing the probiotics (preferably one or more *Bacillus* species) and the nutrient composition or such probiotic food or beverage composition is administered to the person. In the case of a hot food product, spore commitment would be hastened due to the hot temperature of the food (preferably in a temperature range of 42° C. to 100° C., including any individual temperature or subrange therein). In the case of a cold or room temperature food product, spores would commit to germination at human body temperature. In either case, spores would commit before or soon after consumption, but preferably would be in a metastable or activated state (in which the spores are neither dormant nor in the vegetative growth phase, but still retain spore-associated resistance to stomach conditions) while in the stomach and would germinate soon after passing into the small intestine to become active, vegetative bacteria, preferably while still in the small intestine. Using compositions and methods according to preferred embodiments of the invention allows the majority of the probiotic bacteria to survive the stomach but also be fully vegetative or become fully vegetative once in the small intestine and to reach the fully vegetative state sooner than if no nutrient germinant composition were used. Most preferably at least 90%, more preferably at least 50%, of the bacteria in a dose of probiotic composition survive the stomach to become vegetative in the small or large intestine.

According to another preferred embodiment, a food or beverage product may be mixed with the nutrient composition or the spore composition prior to administering or ingesting and the other of the nutrient or spore compositions may be separately administered or ingested. Most preferably, the other composition is administered or ingested at substantially the same time as administering or ingesting the food or beverage product containing the nutrient composition or the spore composition is administered or ingested.

According to one preferred embodiment, a method of reducing inflammation or treating inflammatory conditions in the gut comprises the following steps: (1) providing a first composition comprising one or more species of *Bacillus* in spore form; (2) providing a second composition comprising a nutrient germinant composition, wherein the nutrient germinant composition preferably comprises (a) one or more L-amino acids, (b) optionally one or more buffers to maintain the pH of the second composition when added to water in a range of around 6-8, (c) optionally D-glucose, D-fructose, or both D-glucose and D-fructose, (d) and optionally a source of potassium ions, wherein the first and second compositions may optionally be premixed together or may be separate; (3) optionally mixing the first and second compositions together, if not premixed; (4) administering to a human or ingesting the first and second compositions. Most preferably, all ingredients in the first composition are GRAS. Most preferably all ingredients in the second composition are GRAS. Most preferably, all in ingredients in both the first and second compositions are GRAS. According to another preferred embodiment, the first and second compositions are premixed together at the point of manufacturing/packaging as a premixed probiotic composition. Most preferably a dose of probiotic composition according to a amounts in preferred embodiments herein is administered or ingested at step 4.

According to another preferred embodiment, the method of reducing inflammation or treating inflammatory conditions in the gut further comprises the following steps: (5) providing a food or beverage product; and (6) mixing the food or beverage product with (a) the first composition to form a first mixed product, (b) the second composition to form a second mixed product or (c) the pre-mixed first and second compositions to form a third mixed product. Most preferably, steps 5 and 6 are carried out prior to step 4. According to another preferred embodiment, the first and second compositions are premixed with a food or beverage composition as a premixed probiotic food or beverage composition and step (6) comprises optionally adding a fluid, such as water or milk, to the premixed food or beverage composition if it is in solid or powdered form to form a third mixed product, which is carried out prior to step 4. According to another preferred embodiment, the method further comprises (7) heating (a) the food or beverage product to a temperature between 42° C. and 100° C. prior to the mixing in step 6 or (b) the first, second, or third mixed product to a temperature between around 42° C. and around 100° C. prior to the administering or ingesting in step 4. According to another preferred embodiment, the method further comprises (8) waiting 2 to 10 minutes (or any number of minutes or subrange therein) after the heating in step 7 and before the administering or ingesting in step 4. According to another preferred embodiment, the temperature in the heating step is preferably between 60° C. and 90° C., more preferably between 70° C. and 85° C.

Most preferably, the administering or ingesting step in step (4) comprises administering to the human or ingesting (a) the first and second compositions at substantially the same time, (b) the premixed first and second compositions, (c) the first mixed product and the second composition at substantially the same time, (d) the second mixed product and the first composition at substantially the same time; or (e) the third mixed product.

According to another preferred embodiment, the first composition in step 1 comprises one or more species of *Bacillus* in spore form or a spore formulation according to preferred embodiments of the invention, but other bacteria compositions may also be used. Preferably, the *Bacillus* species are *Bacillus licheniformis*, or *Bacillus subtilis*, or a combination thereof. More preferably, the *Bacillus* species are two different strains of *Bacillus licheniformis* and at least one strain of *Bacillus subtilis*. Most preferably, the *Bacillus* species comprises around 40% of a first strain of *Bacillus*

*licheniformis*, around 40% of a second strain of *Bacillus licheniformis*, and around 20% of the at least one strain of *Bacillus subtilis*.

According to another preferred embodiment, the second composition in step 2 comprises a nutrient-germinant composition, preferably one according to preferred embodiments of the invention. Most preferably, the second composition comprises one or more L-amino acids, optionally one or more buffers to maintain the pH of the second composition when added to water in a range of around 6-8; optionally D-glucose, D-fructose, or both D-glucose and D-fructose; and optionally a source of potassium ions.

According to another preferred embodiment, a method of reducing inflammation or treating inflammatory conditions in the gut comprises the following steps: (1) providing a probiotic composition comprising a spore composition and a nutrient germinant composition, preferably compositions according to preferred embodiments of the invention; and (2) administering to a human or ingesting a dose of the probiotic composition. Most preferably, all ingredients in the probiotic composition are GRAS. Most preferably all ingredients in the spore composition are GRAS. Most preferably, all ingredients in the nutrient germinant composition are GRAS. Additionally steps may include adding or mixing a food or beverage product and heating to a temperature range as described with other preferred embodiments herein.

The probiotic composition in step 1 preferably comprises around 0.1 to 1% of a spore composition and around 99 to 99.9% of a nutrient germinant composition, both by weight of the probiotic composition. The spore composition comprises one or more species of *Bacillus* in spore form. The nutrient germinant composition comprises (a) one or more L-amino acids, (b) a source of potassium ions, and (c) one or more buffers to maintain the pH of the second composition when added to water or a food or beverage product comprising water in a range of around 6-8, the one or more buffers comprising a phosphate buffer, HEPES, Tris base, or a combination thereof, and wherein the source of potassium ions may also be the one or more buffers. The dose in step 2 is around 1 to 4 g of the probiotic composition, more preferably around 2-3 g of the probiotic composition if a flavoring is included. The dose in step 2 is around 0.1 to 0.8 g of the probiotic composition, more preferably around 0.2 to 0.6 g of the probiotic composition, and most preferably around 0.4 to 0.5 g of the probiotic composition if a flavoring is not included.

Most preferably, the steps are periodically repeated so that a dose of probiotic composition is administered or ingested around 1 to 3 times per day, more preferably around 1 to 2 times per day. Most preferably, the administering or ingesting step is carried out over a treatment cycle of at least 6 months, more preferably at least 4 months. A human receiving the doses of probiotic composition over a treatment cycle will have a first C-reactive protein level prior to beginning the treatment cycle and a second C-reactive protein level at the end of the treatment cycle. The second C-reactive protein level is preferably reduced by at least 10%, more preferably at least 15%, and most preferably at least 20% compared to the first C-reactive protein level. When a person's first level of C-reactive protein is less than around 1,000 pg/mL (typically considered a "healthy" level), second C-reactive protein level is preferably reduced by at least 5%, more preferably at least 10%, and most preferably at least 15% compared to the first C-reactive protein level. When a person's first C-reactive protein level is greater than around 1,000 pg/mL, second C-reactive protein level is preferably reduced by at least 15%, more preferably at least 20%, and most preferably at least 23% compared to the first C-reactive protein level.

To determine the effect of a preferred probiotic composition and method of reducing inflammation according to a preferred embodiment of the invention, a 4 month, double-blind, placebo-controlled, open-label study was performed with approximately 50 subjects. Subjects were screened and randomly allocated to either a probiotic group (or treatment group, n=35) or placebo group (n=15). The subjects in the treatment group had a similar Body Mass Index (BMI) (M=31.73, SD=6.87) to the placebo group (M=30.71, SD=5.74) indicating similar degrees of overall health of both groups. Saliva samples were taken at the start and end of the study and analyzed for C-reactive protein (CRP), a marker for systemic inflammation. Signed, informed consent was obtained from all participants prior to enrollment. No participants were excluded for health reasons.

Participants added one 2 g sachet dose (containing either probiotic powder according to a preferred composition or a placebo powder) to 8 oz. (approx. 237 mLs) of a warm to hot beverage and mixed for approximately 2 minutes prior to consuming the beverage. Participants could use any warm to hot beverage they wanted, such as water, coffee, tea, or hot chocolate. The beverages were heated to a range between 70° C.-85° C., according to participant preference. Each dose in a probiotic sachets contained around $10^8$ CFU's *Bacillus subtilis*, 0.22 g L-alanine, 0.23 g dipotassium phosphate, and 1.55 maltodextrin-based vanilla filler as flavoring. Each does in the placebo sachets contained only 2 g of maltodextrin-based vanilla flavoring. Both treatments were identical in appearance and smell and all ingredients were Generally Recognized as Safe (GRAS). The entire dose (the entire beverage in which the dose of probiotic powder or placebo powder) was consumed within approximately 15 to 60 minutes after mixing and compliance was self-reported. Each participant consumed 1 beverage containing either the probiotic powder or placebo powder according to the participant's group assignment each day over the course of a four month trial period (a treatment cycle). Overall approx. 1-2 doses were missed each month for each group (probiotic and placebo).

Fasting passive drool samples were provided by each participant using a Salimetrics SalivaBio Collection Aid and were frozen in cryovials after collection as suggested by the manufacturer. Samples were collected at time 0, representing a baseline and again after 4 months. CRP was measured using the Salimetrics Salivary C-Reactive Protein (CRP) Enzyme Immunoassay Kit (Generation II), as per manufacturer's instructions. In some cases, samples had to be diluted to obtain accurate results. CRP in pg/mL was determined via standard curve as per the manufacturer's instructions. Data was processed using a paired T-test.

Trial results are presented in Table 1 and statistical analysis (paired t-test) is presented in Table 2. In the treatment group, the mean reduction in CRP (M=411.533, p=0.03) was significantly greater than zero, suggesting that a nutrient-germinant probiotic according to a preferred embodiment of the invention is effective in reducing systemic inflammation. This is compared to the placebo group where the mean reduction was significantly lower (M=57.46, p=0.43), suggesting no change. In both groups, the variance was large; however, a large variance was expected as participants of all levels of health, and therefore degrees of inflammation, were recruited. The same is true for standard deviation.

TABLE 1

Descriptive statistics for treatment and placebo groups at month 0 and month 4 are presented.

|  | Treatment | | Placebo | |
| --- | --- | --- | --- | --- |
|  | Month 0 | Month 4 | Month 0 | Month 4 |
| Mean | 1483.35 | 1071.81 | 1086.82 | 1029.37 |
| Standard Error | 274.24 | 158.88 | 401.54 | 266.40 |
| Standard Deviation | 1622.45 | 939.97 | 1555.17 | 1031.77 |
| Sample Variance | 2632340.26 | 883537.99 | 2418545.01 | 1064549.92 |
| Skewness | 1.51 | 1.12 | 2.52 | 1.19 |
| Range | 6409.44 | 3366.11 | 5882.83 | 3337.70 |
| Minimum | 69.89 | 70.11 | 86.50 | 64.63 |
| Maximum | 6479.33 | 3436.22 | 5969.33 | 3402.33 |
| Count | 35 | 35 | 15 | 15 |

TABLE 2

Results of a paired t-test for reduction in systemic inflammation suggest a decrease in inflammation. Due to the skew in the positive direction (Table 1) for both treatment and placebo groups, a one-tailed p-value is reported.

|  | Treatment | Placebo |
| --- | --- | --- |
| Mean reduction | 411.53 | 57.46 |
| Observations | 35 | 15 |
| Hypothesized Mean Difference | 0 | 0 |
| t Stat | 1.87 | 0.19 |
| P(T<=t) one-tail | 0.03 | 0.43 |
| t Critical one-tail | 1.69 | 1.76 |

As used herein, ingested (or variants thereof) means to be orally ingested. As used herein, administered (or variants thereof) means any form of administering directly into the stomach (such as through a feeding tube) or digestive tract, unless a specific form of administration is specified. As used herein consumed (or variants thereof) means ingested and/or administered. Nutrient compositions, spore compositions, and optional food or beverage products according to the embodiments of the invention may be separately administered or ingested or may be premixed together in any combination prior to being administered or ingested. Additionally, nutrient compositions, spore compositions, and optional food or beverage products according to the embodiments of the invention may be in solid or powered form, liquid form, or other fluid form (such as thickened products, like yogurt or gravy or pudding) or may be separately in any combination of such forms to be mixed together in any combination prior to administration or ingestion or to be administered or ingested at substantially the same time. As used herein "substantially the same time" means (1) in sequential order, one component right after the other; or (2) each component is administered or ingested within less than around 60 seconds of the previous component or components being administered or ingested.

All amounts for ingredients or ratios of ingredients, numeric values, temperature, or duration/time indicated herein as a range include each individual amount/value or ratio within those ranges and any and all subset/subrange combinations within ranges, including subsets/subranges that overlap from one preferred range/subrange to a more preferred range/subrange. References to ounces herein are fluid ounces. Any ingredient, amount, numeric value, or step described with one preferred embodiment herein may also be used with any other preferred embodiment herein, even if not expressly described with such embodiment unless it is expressly excluded for that embodiment. Those of ordinary skill in the art will appreciate upon reading this specification, including the examples contained herein, that modifications and alterations to the composition and methodology for making the composition may be made within the scope of the invention and it is intended that the scope of the invention disclosed herein be limited only by the broadest interpretation of the appended claims to which the inventor is legally entitled.

We claim:

1. A method of reducing inflammation or treating inflammatory conditions in the gut of a human, the method comprising:

heating a probiotic composition to a temperature in a range between around 70° C. and around 85° C., the probiotic composition comprising around 0.025 to 1% of a spore composition and around 99 to 99.9% of a nutrient germinant composition, both by weight of the probiotic composition;

consuming a dose of around 1 to 4 g of the heated probiotic composition at least one time per day over a treatment cycle of at least 4 months;

wherein the spore composition comprises one or more species of *Bacillus* in spore form;

wherein the nutrient germinant composition comprises (a) one or more L-amino acids, (b) a source of potassium ions, and (c) one or more buffers, if the source of potassium ions is not a buffer, to maintain the pH of the probiotic composition when added to water in a range of around 6-8, the one or more buffers comprising a phosphate buffer, HEPES, Tris base, or a combination thereof;

wherein all ingredients in probiotic composition are GRAS; and wherein the human has a first C-reactive protein level prior to beginning the treatment cycle and a second C-reactive protein level at the end of the treatment cycle, and wherein the second C-reactive protein level is reduced by at least 10% compared to the first C-reactive protein level.

2. The method of claim 1 wherein the heating stew comprises heating a premixed probiotic food or beverage composition comprising the dose of the probiotic composition and a food or beverage product; and wherein the consuming step comprises consuming the heated premixed probiotic food or beverage composition.

3. The method of claim 2 wherein the premixed probiotic food or beverage composition is in solid or powered form, the method further comprising:

mixing a potable fluid with the premixed probiotic food or beverage composition to form a fluid probiotic food or beverage composition;

wherein the heating step comprises heating the fluid probiotic food or beverage composition; and wherein the administering to the human or ingesting step comprises administering to a human or ingesting the heated fluid probiotic beverage composition.

4. The method of claim 3 wherein the food or beverage product comprises coffee, tea, hot chocolate, or soup.

5. The method of claim 4 wherein (1) the second C-reactive protein level is reduced by at least 10% compared to the first C-reactive protein level when the first level of C-reactive protein is less than around 1,000 pg/mL or (2) the second C-reactive protein level is reduced by at least 20% compared to the first C-reactive protein level when the first level of C-reactive protein is around 1,000 pg/mL or higher.

6. The method of claim 1 wherein the consuming step comprises consuming a probiotic food or beverage composition comprising the dose of the probiotic composition, the method further comprising:
mixing the probiotic composition and a food or beverage product together to form the probiotic food or beverage composition; and
wherein the heating step comprises (1) heating the food or beverage product to the temperature range prior to the mixing step or (2) heating the probiotic food or beverage composition to the temperature range after the mixing step.

7. The method of claim 6 further comprising waiting for 2 to 10 minutes after the heating step before the consuming step.

8. The method of claim 6 wherein the nutrient germinant composition comprises (a) around 40 to 45% of the one or more amino acids, (b) around 40 to 45% of the source of potassium ions, and (c) around 10 to 20% of the one or more buffers if separate from the source of potassium ions, by weight of the nutrient germinant composition.

9. The method of claim 8 wherein the spore composition comprises $10^7$ to $10^{10}$ spores/g of *Bacillus subtilis* and the nutrient germinant composition comprises around 40 to 45% L-alanine and around 40 to 45% dipotassium phosphate as the source of potassium ions and the buffer, by weight of the nutrient germinant composition.

10. The method of claim 9 wherein the probiotic composition does not contain potassium chloride.

11. The method of claim 9 wherein the nutrient germinant composition further comprises an osmoprotectant.

12. The method of claim 6 wherein the spore composition and nutrient germinant composition are separate and the method further comprises mixing the spore composition and the nutrient germinant composition together prior to mixing with the food or beverage product.

13. The method of claim 1 wherein the nutrient germinant composition comprises (a) around 40 to 45% of the one or more amino acids, (b) around 40 to 45% of the source of potassium ions, and (c) around 10 to 20% of the one or more buffers if separate from the source of potassium ions, all by weight of the nutrient germinant composition.

14. The method of claim 13 wherein the spore composition comprises $10^7$ to $10^{10}$ spores/g of *Bacillus subtilis* and the nutrient germinant composition comprises around 45 to 55% L-alanine and around 45 to 55% dipotassium phosphate as the source of potassium ions and the buffer, by weight of the nutrient germinant composition.

15. The method of claim 14 wherein the probiotic composition does not contain potassium chloride.

16. The method of claim 14 wherein the nutrient germinant composition further comprises an osmoprotectant.

17. A method of reducing inflammation or treating inflammatory conditions in the gut, the method comprising:

providing a heated probiotic food or beverage composition comprising (1) a dose of around 1 to 4 g of a probiotic composition comprising around 0.025 to 1% of a spore composition and around 99 to 99.9% of a nutrient germinant composition, both by weight of the probiotic composition and (2) a food or beverage product, wherein the providing step comprises (a) providing the probiotic food or beverage composition as a pre-mixed composition and heating the pre-mixed composition to a temperature between around 70° C. and around 85° C., (b) heating the food or beverage product to a temperature between around 70° C. and around 85° C. and then mixing the probiotic composition and the heated food or beverage product together, or (c) mixing the probiotic composition and the food or beverage product together and then heating the mixture to a temperature between around 70° C. and around 85° C.;
administering to a human the heated probiotic food or beverage composition;
periodically repeating the administering step at least 1 time per day;
wherein the spore composition comprises one or more species of *Bacillus* in spore form;
wherein the nutrient germinant composition comprises (a) around 40 to 45% of one or more L-amino acids, (b) around 40 to 45% of a source of potassium ions, and (c) around 10 to 20% of one or more buffers if separate from the source of potassium ions, to maintain the pH of the second composition when added to water or a food or beverage product comprising water in a range of around 6-8, the one or more buffers comprising a phosphate buffer, HEPES, Tris base, or a combination thereof, and wherein the source of potassium ions may also be the one or more buffers, and wherein the percentages are by weight of the nutrient germinant composition;
wherein all ingredients in probiotic composition are GRAS;
wherein the administering step is carried out over a treatment cycle of at least 4 months, wherein the human has a first C-reactive protein level prior to beginning the treatment cycle and a second C-reactive protein level at the end of the treatment cycle, and wherein the second C-reactive protein level is reduced by at least 10% compared to the first C-reactive protein level.

18. The method of claim 17 wherein the human has ulcerative colitis or Crohn's disease.

19. The method of claim 17 wherein the administering step comprises supplying the heated probiotic food or beverage composition to the human through a feeding tube.

20. The method of claim 17 wherein the administering step comprises the human orally ingesting the heated probiotic food or beverage composition.

* * * * *

UNITED STATES PATENT AND TRADEMARK OFFICE
CERTIFICATE OF CORRECTION

PATENT NO. : 11,576,937 B2
APPLICATION NO. : 17/170048
DATED : February 14, 2023
INVENTOR(S) : Gabriel F. K. Everett et al.

It is certified that error appears in the above-identified patent and that said Letters Patent is hereby corrected as shown below:

On the Title Page

Item (54) and in the Specification Column 1, Lines 1-4, the title should be corrected to:
METHOD OF REDUCING GUT INFLAMMATION IN HUMANS BY CONSUMING A HEATED PROBIOTIC COMPOSITION Signed and Sealed this
Eighteenth Day of April, 2023

Katherine Kelly Vidal
*Director of the United States Patent and Trademark Office*